United States Patent
Wei et al.

(10) Patent No.: US 12,077,814 B2
(45) Date of Patent: Sep. 3, 2024

(54) METHOD FOR LOW FREQUENCY SOMATIC CELL MUTATION IDENTIFICATION AND QUANTIFICATION

(71) Applicant: PEKING UNIVERSITY, Beijing (CN)

(72) Inventors: Liping Wei, Beijing (CN); Boxun Zhao, Beijing (CN); Yue Huang, Beijing (CN); Qixi Wu, Beijing (CN); Yongxin Ye, Beijing (CN); Xianing Zheng, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 965 days.

(21) Appl. No.: 16/616,865

(22) PCT Filed: Jul. 23, 2018

(86) PCT No.: PCT/CN2018/096620
§ 371 (c)(1),
(2) Date: Nov. 25, 2019

(87) PCT Pub. No.: WO2018/214989
PCT Pub. Date: Nov. 29, 2018

(65) Prior Publication Data
US 2023/0265496 A1    Aug. 24, 2023

(30) Foreign Application Priority Data
May 25, 2017    (CN) .......................... 201710381726.8

(51) Int. Cl.
*C12Q 1/6869*    (2018.01)
*C12N 15/10*    (2006.01)
(Continued)

(52) U.S. Cl.
CPC ....... *C12Q 1/6869* (2013.01); *C12N 15/1093* (2013.01); *C12Q 1/6883* (2013.01);
(Continued)

(58) Field of Classification Search
None
See application file for complete search history.

(56) References Cited

U.S. PATENT DOCUMENTS 8,071,310 B2    12/2011    van Eijk et al.
2009/0208943 A1    8/2009    van Eijk et al.
(Continued)

FOREIGN PATENT DOCUMENTS

CN    101310024 A    11/2008
CN    102628083 A    8/2012
(Continued)

OTHER PUBLICATIONS

Burns et al Cell. 2012. 149(4): 740-752 (Year: 2012).*
(Continued)

*Primary Examiner* — Carla J Myers
(74) *Attorney, Agent, or Firm* — Harness, Dickey & Pierce, P.L.C.

(57) ABSTRACT

A method for low frequency somatic cell mutation identification and quantification, relating specifically to a method for transposon copy number and genome location identification. Specific sites of different transposon families are used, transposon insertion sequences are specifically enriched via library construction, high-throughput sequencing and bioinformatics analysis are used, and genome locations, copy numbers and types of transposons within samples are accurately identified. The method economically and accurately identifies copy numbers and genome locations of transposons.

19 Claims, 6 Drawing Sheets
Specification includes a Sequence Listing.

(51) Int. Cl.
*C12Q 1/6883* (2018.01)
*C12Q 1/6886* (2018.01)

(52) U.S. Cl.
CPC ...... *C12Q 1/6886* (2013.01); *C12Q 2600/118* (2013.01); *C12Q 2600/156* (2013.01)

(56) References Cited

U.S. PATENT DOCUMENTS

2013/0143746 A1* 6/2013 Xue .................. C12N 15/1093
506/26
2016/0275240 A1* 9/2016 Huelga ................ C12Q 1/6806

FOREIGN PATENT DOCUMENTS

| CN | 103757014 A | 4/2014 |
| CN | 105524920 A | 4/2016 |
| WO | WO-2016033251 A2 | 3/2016 |

OTHER PUBLICATIONS

Poduri et al Science. 2013. 341(6141): 1237758, p. 1-16 (Year: 2013).*

Wilkie, G., "Illumina Adapter and Primer Sequences," [http://bioinformatics.cvr.ac.uk/blog/illumi.na-adapter-and-primer-sequences/], Jan. 26, 2015 (Jan. 26, 2015), pp. 1-7.

Goodman, A. L., et al., "Identifying Genetic Determinants Needed to Establish a Human Gut Symbiont in Its Habitat," Cell Host & Microbe, vol. 6, Sep. 17, 2009 (Sep. 17, 2009), pp. 279-289.

International Search Report (in English and Chinese) and Written Opinion (in Chinese) of the International Searching Authority issued in PCT/CN2018/096620, mailed Oct. 24, 2018; ISA/CN.

* cited by examiner

Representative ACC1 specific insertion site
ACC1_132 (chr21:29069165)

METHOD FOR LOW FREQUENCY SOMATIC CELL MUTATION IDENTIFICATION AND QUANTIFICATION

CROSS REFERENCE TO RELATED APPLICATIONS

This application is the national phase of International Application No. PCT/CN2018/096620, titled with "METHOD FOR LOW FREQUENCY SOMATIC CELL MUTATION IDENTIFICATION AND QUANTIFICATION", which claims the priority of Chinese Patent Application No. 201710381726.8, filed on May 25, 2017, and titled with "METHOD FOR LOW FREQUENCY SOMATIC CELL MUTATION IDENTIFICATION AND QUANTIFICATION", and the disclosures of which are hereby incorporated by reference.

This application contains references to amino acid sequences and/or nucleic acid sequences which have been submitted concurrently herewith as the sequence listing text file entitled "000675usnp_SequenceListing.TXT", file size 3,851 bytes, created on May 29, 2024. The aforementioned sequence listing is hereby incorporated by reference in its entirety pursuant to 37 C.F.R. § 1.52(e)(5).

FIELD

The present invention relates to the field of genetic testing, specifically to the identification and quantification of low frequency mutations in genome, for example the detection of de novo transposon insertion event.

BACKGROUND

Transposon, also known as transposable element, is a basic unit capable of autonomously replicating and changing location on chromosomal DNA. In addition to being abundantly present in the genome, a transposon can replicate or transpose its own sequence to a new genomic locus at a certain frequency in an individual. This transposition event may affect the phenotype. For example, a transposition event that results in the inactivation of a functional gene may cause diseases (especially for Mendelian disorders). Therefore, the identification of transposition events has important clinical significance for disease pathogenesis research, genetic counseling, diagnosis and prognosis evaluation.

Depending on the nature of the transposition, transposons are usually divided into two classes. The first type of transposon is called DNA transposon, which jumps in a "cut-and-paste" manner. After transposition of this type of transposon, the total copy number of the transposon in the genome is unchanged. The second type of transposon is called retrotransposon, which jumps in a "copy-and-paste" manner. The transposon is first transcribed into mRNA, then the mRNA is reinserted into the genome and reverse transcribed back to DNA to complete the retrotransposition process. This means that for every retrotransposition, the copy number of the transposon in the genome is increased by one. The retrotransposon can be further classified into two types: LTR and non-LTR retrotransposons, the former having a long terminal repeat (LTR), and the latter does not have this structure feature.

Based on the autonomy of the transposition, transposable elements are further divided into autonomous transposons and non-autonomous transposons. The former can encode transposase to facilitate its transposition, such as the LINE-1 transposon family; the latter requires the presence of an autonomous transposon to complete the transposition by using the transposase, such as the Alu and SVA transposon families.

LINE-1 (Long INterspersed Element-1), or L1 for short, is the primary transposon in mammals and also the only active autonomous transposon in humans. LINE-1 is a non-LTR type retrotransposon with a length of approximately 6 kb. There are more than 500,000 copies of the LINE-1 sequence in the human genome, but most of them are inactive, and only about 80-100 full-length L1 are capable of active retrotransposition.

There are two types of transposition events for LINE-1: germline insertion and somatic insertion. The former occurs in the parental germline cells and is therefore inherited to and present in all cells of the offspring. In contrast, somatic insertion occurs after the formation of zygotes, from the early embryonic development to the differentiation and maturation stages of somatic cells, thus exists in a proportion of cells within the individual. Therefore, the somatic insertion is also called de novo insertion or cell-specific insertion. In humans, the frequency of somatic mutation is quite low, but it can lead to a variety of diseases, such as cancer, proliferative diseases, nervous system diseases. Therefore, the detection of de novo insertions is of great importance.

At present, there are still many technical difficulties in the identification of de novo somatic transposition.

First, the de novo insertion has no sequence specificity. The newly inserted transposon is not different in sequence from the inherent germline transposon insertions in the genome, which makes it impossible to distinguish the two types of transposition events by investigating the sequence itself.

Second, the background noise is extremely high. As described above, germline transposons are abundantly present in the genome in every single cell, whereas de novo insertions merely account for a very small proportion of all transposons. In other words, when detecting a de novo insertion, the new event must be identified and distinguished from a large copy number of the endogenous germline insertions in the genome. In addition, in a tissue sample to be tested, there may be only a few cells carrying a specific clonal insertion, which means that the signal for a de novo insertion in the sample is reduced by $10^2$ to $10^3$. Owing to the rarity of de novo insertion, a very large number of cells need to be sequenced to ensure that cells containing de novo insertion are sampled in the test sample. It is financially impossible to perform single cell sequencing approach to exclude the interference from a large number of reference cells in a sample. In summary, the detection of de novo insertion must effectively eliminate the high background noise from a large number of other cells as well as the high background noise caused by the inherited germline transposon sequences in the cells carrying de novo insertion.

In addition, current sequencing methods typically first use PCR to amplify the sequences and then sequence the amplified product. During the exponential PCR amplification process, there is a competition between different templates for the reaction substrate, and the germline insertion with a high copy number has a higher chance of being amplified. Such enrichment method would greatly amplify the germline insertion, causing the relative signal intensity of the low frequency de novo insertion to be further attenuated. If nested PCR is used, the above trend will be further enhanced.

Moreover, the high-throughput sequencing currently used, also known as next generation sequencing (NGS), generally uses a sequencing-by-synthesis high-throughput sequencing scheme. For example, in the commonly used Illumina sequencing method, four bases are labeled with different fluorescence, and a large number of sequence fragments located on the same chip are simultaneously extended by one base per round, using the fluorescent signals in different positions in each round to obtain sequence information. This approach relies on different fluorescent signals at various positions after each round of extension as the basis for a high-throughput analysis algorithm. However, for the sequencing of PCR amplicons, since the sequences in the amplicon are highly uniform, the fluorescence signals of each position are almost the same after each round of extension on the chip, and this will result in the instrument not being able to accurately analyze the image data and sequencing errors may occur.

The Salk Institute of the United States has proposed a method for quantitative analysis of transposon copy number change using Taqman qPCR (Coufal, N G et al. L1 retrotransposition in human neural progenitor cells. Nature 460, 1127-1131, doi: 10.1038/nature08248 (2009)). This method quantifies the transposon copy number in different cells and it is presumed that de novo transpositions have occurred in the cells with increased copy number. However, due to the large number of endogenous germline transposon insertions, changes in the copy number of new insertions in somatic cells are easily covered by random fluctuations in the experiment background, resulting in poor experimental repeatability. This method is unable to distinguish between de novo insertions and germline insertions, therefore it cannot specifically identify and characterize de novo insertions, so it is impossible to carry out subsequent functional studies of the insertion events.

Therefore, there is an urgent need in the art for new methods to identify de novo transposition and improve detection limits and accuracy. In addition, there is a need in the art for methods that can specifically identify and characterize de novo insertions.

SUMMARY

The present disclosure provides a method for highly specifically and sensitively identifying the genomic location, copy number and type of a transposon, referred to as Human Active Transposon sequencing, HAT-seq. In particular, the method of the present disclosure is used to specifically identify cell-specific de novo transposon insertion events in the genome. The method of the present disclosure can be used to identify pathogenic transpositions.

More generally, the method of the present disclosure provides a universal detection platform for detecting low-frequency similar sequences in a large number of sequence samples. The application of this method is not limited to de novo transpositions, but can be used universally to identify other low-frequency mutation events, such as SNPs.

In some embodiments, genomic DNA is broken into DNA fragments, which are ligated to adaptors, and then primers are designed for targeting the transposon specific sequence and the adaptor sequence, thereby enriching specific transposon family and incorporating the position information of transposon insertions into the library.

In some embodiments, the use of special library sequence structure combined with nucleotides shifting allows the generation of a mixed high-diversity amplicon library with different phase, which improves the base calling accuracy of Illumina sequencer for the amplicon library sequencing.

In some embodiments, by using high throughput sequencing and bioinformatics analysis, the genomic location and orientation of a transposon is determined. Using the genomic location information of the insertion events, the endogenous germline insertions and the de novo insertions can be distinguished. Thus, using the endogenous germline insertions with known constant copy number as the internal references, an accurate quantification for the de novo insertions can be achieved.

In some embodiments, using the one-tube protocol, all steps are completed in the same container from sample DNA fragmentation to the library construction, ensuring that the de novo insertion signal is not lost during library construction.

In some embodiments, the method comprises a step of isolating DNA from a sample. The sample may be any test cells associated with the intended application. The test cells may be human cells. The test cells may be cells from any tissues, such as stem cells, including but not limited to embryonic stem cells, neural stem cells; somatic cells, including but not limited to cells of liver, heart, brain and blood; nerve cells, including but not limited to neural progenitor cells, neurons, and the like; other disease-related cells, including but not limited to tumor cells.

In some embodiments, the method comprises a step of isolating DNA from a reference sample. The reference sample may be any reference cells associated with the intended application. The reference cells may be human cells.

In some embodiments, the method comprises a step of fragmenting a DNA sample to obtain a DNA fragment library. Fragmentation may be carried out according to any known methods in the art, including but not limited to mechanical treatment (e.g., sonication), enzymatic treatment, and the like.

In some embodiments, the method comprises ligating adaptors to both ends of the fragmented DNA in a DNA library to obtain a transposon-adaptor library.

In some embodiments, the transposon-adaptor library is amplified. In some embodiments, PCR is used for the amplification. In some embodiments, a first primer and a second primer are used for the PCR amplification, wherein the first primer comprises a transposon-specific sequence capable of hybridizing to an internal sequence of the transposon, a second primer comprises an adapting sequence capable of hybridizing to the adaptor, so as to amplify the transposon as well as the flanking sequence thereof. In some embodiments, the transposon-specific sequence is capable of hybridizing to the internal sequence near 3' or 5' end of the transposon. In some embodiments, the transposon specific sequence covers and binds to a target transposon family specific nucleotide or motif. In some embodiments, the transposon specific sequence is capable of hybridizing to an internal sequence of no more than about 5, 10, 20, 30, 40, 50, 60, 70, 80, 90, 100, 110, 120, 130, 140, 150, 160, 170, 180, 190, 200, 210, 220, 230, 240 or 250 bp from the 3' or 5' end of the transposon.

In some embodiments, the amplified products are subjected to sequencing to obtain flanking sequences. In some embodiments, the sequencing is performed by a high-throughput sequencing method. All the sequencing methods known in the art can be used, such as Illumina sequencing or Ion Torrent sequencing.

In some embodiments, the obtained flanking sequence is aligned with a reference genomic sequence to obtain genomic location and orientation of the transposon. In some embodiments, the reference genome is a human reference genome.

In some embodiments, the genomic location of transposon obtained from the test sample is compared with the genomic location of transposon obtained from the reference sample to identify a transposon insertion event which shows difference in genomic location between the test sample and the reference sample. A transposon insertion event present in the test sample but absent in the reference sample will be identified as a cell-specific insertion.

In some embodiments, the total number of sequences derived from tissue or cell specific transposon insertions, and the total number of sequences derived from the germline transposon insertions in the reference genome of the subject are counted respectively, and the ratio of the two numbers is calculated to quantify the tissue or cell specific transposon insertion. In some embodiments, the transposon for identification is a LINE-1 transposon, such as a subfamily L1Hs of the human LINE-1 transposon.

The method of the present disclosure has extremely high detection sensitivity and specificity, making it possible to identify single-cell level de novo transposon insertions and the copy number changes from a bulk DNA sequencing data for the first time.

BRIEF DESCRIPTION OF DRAWINGS

In FIG. 4A, M represents Marker, A represents the PCR product of ACC1, Z represents the PCR product of ZBX, and NTC represents a negative control. Representative site numbers are shown in FIG. 4B, and for each site, the PCR products of ACC1 and ZBX are loaded successively. Marker=100 bp ladder.

DETAILED DESCRIPTION

Figure 1:
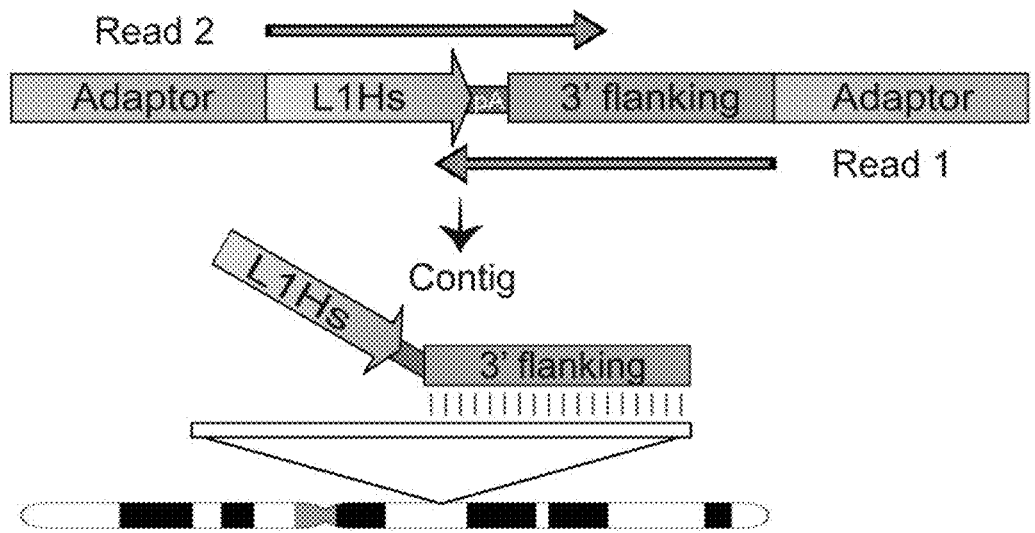
FIG. 1 is a schematic diagram showing an amplicon with adaptors at both the 5' and 3' ends in one embodiment. When the library is sequenced, the sequences (read 1 and read 2) are generated from the two adaptors in the 5' to 3' direction, respectively, thereby obtaining the 3' flanking sequence of L1Hs insertions, which contains genomic location information.

Transposons are important components of a genome. One-third of the human genomic sequence belongs to retrotransposons, which cause de novo insertion events at a certain frequency. In germ cells, if a de novo insertion affects the function of a gene, it can lead to the occurrence of genetic diseases. In somatic cells, transposons have been shown to undergo transposition in embryonic stem cells, neural progenitor cells, mature neurons, and tumor cells. Therefore, transposon insertion events may participate in and affect the entire process of tissue development and tumorigenesis. In different tissues, the frequency of transposition is different, which is especially high in the brain, suggesting that transposon insertion events may contribute to neuronal polymorphism. Under different physiological and pathological conditions, the frequencies of transposition are different. Transposons have been shown to have more copies in Rett syndrome, schizophrenia, and Alzheimer's disease patients, suggesting that transposon insertion events may contribute to susceptibility to neuropsychiatric disorders and disease development.

Amplification of LINE-1 Flanking Sequence

In cells in which a de novo insertion occurs, the sequence of the de novo transposon insertion is identical to the endogenous inactive transposons and thus cannot be distinguished. The inventors propose that although the transposon sequence of the de novo insertion is identical to the endogenous germline insertion, the de novo insertion would appear in new genomic location. Thus, compared to a reference cell, a transposon that appears on a new genomic location is a de novo transposon insertion. If the position of the transposon sequence in the genome can be located, the de novo transposition can be identified thereby.

Therefore, it is necessary to obtain the flanking sequence of the transposon and align it with the genomic sequence to obtain the location. However, the genomic location and sequence exterior to the de novo transposon insertions are unknown, so the flanking sequences cannot be targeted and amplified for sequencing with conventional primer design.

In some embodiments, the genomic DNA is first fragmented and then the ends of the DNA fragments are blunted and A (deoxyadenosine triphosphate, dATP) is added at the 3' end, and then the fragments are ligated to an adaptor, such as an Illumina library adaptor. PCR is performed using primers targeting the LINE-1 specific sequence and the adaptor, respectively, thereby amplifying LINE-1 together with the flanking sequence thereof to give amplicons. LINE-1 and the flanking sequence thereof can then be sequenced using high-throughput sequencing technologies.

In some preferred embodiments, the 5' primer for PCR is adaptor 1 (e.g., P7 adaptor)+LINE-1 specific sequence, and the 3' primer is adaptor 2 (e.g., P5 adaptor) sequence. Thus, the structure of the resulting amplicon is: adaptor 1—LINE-1 specific sequence—flanking sequence—adaptor 2 sequence. Both the 5' and 3' ends of the amplicon contain an adaptor sequence, so the amplicon can be sequenced in the 5' and 3' directions from the two adaptor sequences, respectively. The length of fragments that can be effectively sequenced with high throughput sequencing technologies such as Illumina is typically very limited, for example 100-200 bp. This paired-end sequencing design significantly extends the effective sequencing length and allows the two sequencing results to be cross-checked to greatly improve sequencing accuracy.

The adaptors used in the methods of the present disclosure may be adaptors well known in the art, such as the Illumina library P5, P7 adaptors, the adaptors of the Ion Torrent library.

FIG. 1 shows the design of the amplicon in a preferred embodiment. In FIG. 1, the sequences from both ends are spliced together using the overlapping portion of the sequences obtained by paired-end sequencing to form a contig that completely spans the transposon insertion—genome junction. The L1Hs sequence information (read 2) is used to screen the L1Hs data that is correctly amplified; the 3' flanking sequence (read 1) is used for mapping with the reference genome to obtain the location and orientation of the insertion event in the genome.

Nucleotides Shifting

As described above, when PCR amplicons are subjected to high-throughput sequencing, since the sequences of the amplicon are identical, the incorporated bases for each round of extension on the chip are the same, resulting in the same fluorescent color at most points of the chip, which seriously affect the quality of sequencing. To solve this problem, the inventors introduced several random sequences between the 5' adaptor and the LINE-1 specific sequence in the primer, resulting in the effect of nucleotides shifting. In this way, the LINE-1 specific sequence starts at a different position in different primers. Therefore, in the sequencing process initiated by sequencing primers, the incorporated bases in each sequencing cycle are no longer the same, but random, thereby avoiding the occurrence of a single fluorescent signal on the sequencing chip which seriously affects the quality of sequencing. The length and sequence of the introduced random region are not particularly limited, as long as the positions of the LINE-1 specific sequence on different primers can be made different. For example, a random region of 1, 2, 3, 4, 5, 6, 7, 8, 9, 10, 11, 12, 13, 14, 15, 16, 17, 18, 19 or 20 bp may be independently introduced into different primers.

Figure 2:
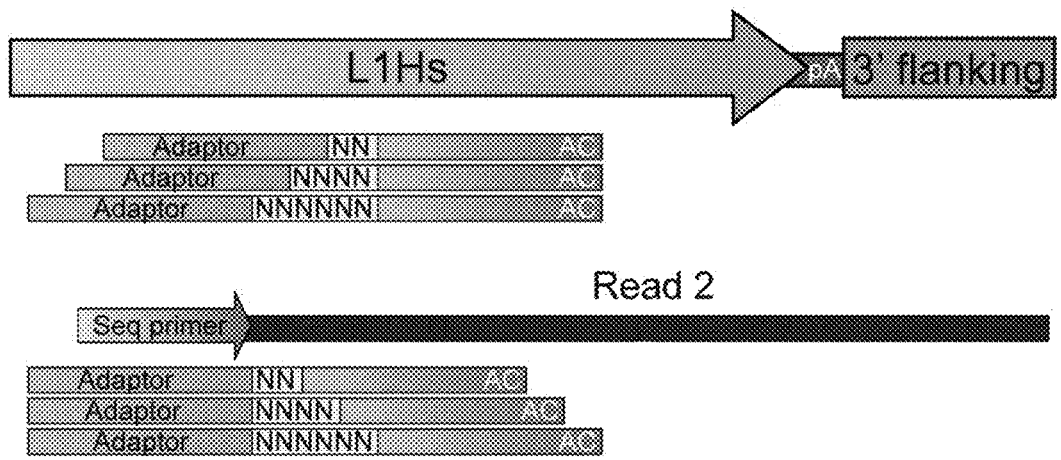
FIG. 2 is a set of primers used in one embodiment for nucleotides shifting design. The amplicons produced by these primers will be added with different bases in the same round of extension of the sequencing cycle.

FIG. 2 shows the 5' primer design in one embodiment. The upper panel shows in three different primers, a random sequence of 2, 4, and 6 bases are introduced between the adaptor and the LINE-1 specific sequence. The lower panel is a schematic diagram of the library under sequencing, in which the Seq primer is the binding site for sequencing primer and the dark gray strip is a 150 bp reading of sequence information.

Sequencing Data Processing

The amplicon library is sequenced by high throughput sequencing. Based on the output of the sequencing results, the flanking sequences are aligned with a reference genome (e.g. a human reference genome), and each LINE-1 sequence is mapped to a corresponding position in the genome, thereby obtaining a map of positions for all the LINE-1 transposons in the test genome. The LINE-1 position map of the test cells is compared with that of the reference cells, and the LINE-1 locus not existent in the reference cells is a de novo insertion. Thereby, a specific position of a de novo insertion in the genome where occurs can be obtained.

Further, the ratio of de novo insertions to endogenous germline insertions in the sample can be calculated and the copy number of the de novo insertions can be determined based on the copy number of endogenous germline insertions.

EXAMPLES

Example 1 Detection of ACC1 Individual-Specific Germline Transposon Insertion Event Step 1: Isolating Sample DNA In this example, a blood sample taken from a healthy subject 1 (a healthy adult from the laboratory, sample code ACC1) was subjected to DNA extraction using a DNA extraction kit (Qiagen, Cat. 51104) to obtain the DNA from plasma.

Step 2: Constructing DNA Library for Paired-end Sequencing 500 ng of genomic DNA was sonicated using Covaris S220 under the following conditions: sample volume (μl) 50, water level 12, temperature (° C.) 7, peak incident power (W) 175, duty factor 5%, cycles per burst 200, treatment duration (s) 55. The ends of extracted DNA were made blunt using the library construction kit (KAPA Biosystems, Cat. KK8232), and A was added to the 3' end and then the adaptor was ligated.

P5_adaptor
(5'-ACACTCTTTCCCTACACGACGCTCTTCCGATC*T-3' (SEQ ID NO: 1)), and

P7_truncated
(5'(P)-GATCGGAAGAGC*A*C-3' (SEQ ID NO: 2)).

wherein * indicates phosphorothioate modification, and (P) represents phosphorylation modification.

20 ng DNA (corresponding to approximately 3,000 cells) with adaptors was used as a template for PCR enrichment.

Figure 3:
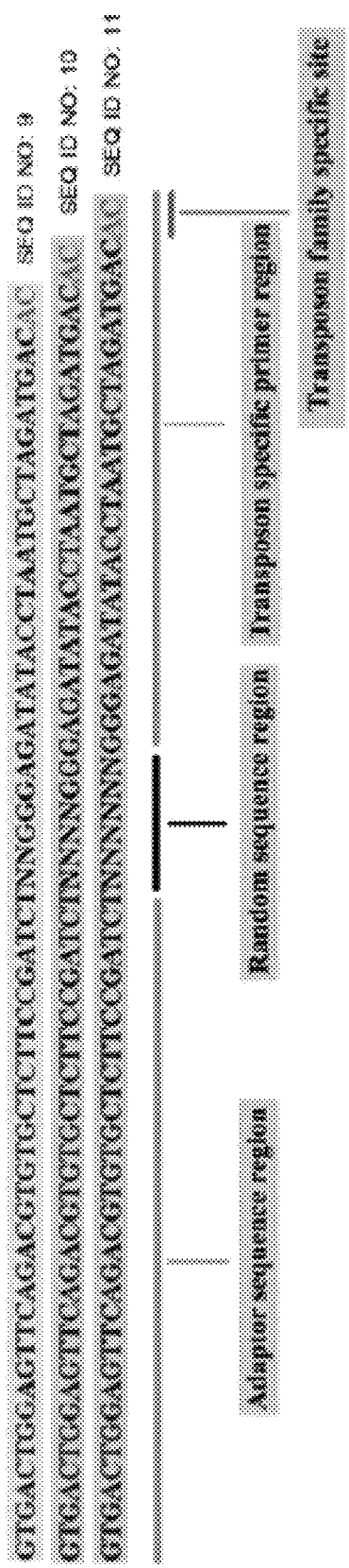
FIG. 3 is specific sequences of a primer set for nucleotides shifting design in one embodiment.

Step 3: Enriching Transposon Insertion Events from DNA Paired-end Sequencing Library Primers were designed based on the specific sequence of the LINE-1 family, which was set at the 3' end of the primers. The primer structure is shown in FIG. 3, where the adaptor sequence region, the random sequence region and the transposon family-specific primer sequence region are sequentially presented from 5' end to 3' end direction.

PCR protocol: 12.5 μl KAPA2G Robust HotStart ReadyMix (2×) (KAPA Biosystems, KK5702), 1.25 μl P7_Ns_L1 Primer (10 μM), water was added to make up to 23.75 μl. After linear amplification, 1.25 μl of another primer was added:

P5_extension (10 µM) (5'-

```
AATGATACGGCGACCACCGAGATCTACACTCTTTCCCTACACGACGC-3'
(SEQ ID NO: 3)).
```

PCR program:

| | | |
|---|---|---|
| 95° C. Denature 5 min | | |
| 95° C. 40 s | | 5 Cycles |
| 61° C. 15 s | | |
| 72° C. 15 s | | |
| 12° C. Pause | | Add P5_extension |
| 95° C. 40 s | | 11 Cycles |
| 61° C. 15 s | | |
| 72° C. 15 s | | |
| 72° C. 30 s | | |
| 4° C. Hold | | |
| 1.05 × Agencourt AMPure XP Beads (Beckman) Treatment | | |

P7_Ns_L1 (10 µM) used in PCR is an equimolar mixture of the following three primers:

```
P7_N2_L1
(5'-GTGACTGGAGTTCAGACGTGTGCTCTTCCGATCTNNGGGAGATAT
ACCTAATGCTAGATGAC*A*C-3' (SEQ ID NO: 4)),

P7_N4_L1
(5'-GTGACTGGAGTTCAGACGTGTGCTCTTCCGATCTNNNNGGGAGAT
ATACCTAATGCTAGATGAC*A*C-3' (SEQ ID NO: 5)), and P7_N6_L1
(5'-GTGACTGGAGTTCAGACGTGTGCTCTTCCGATCTNNNNNNGGGAG
ATATACCTAATGCTAGATGAC*A*C-3' (SEQ ID NO: 6)),
``` wherein * indicates phosphorothioate modification.

Step 4: Sequencing the Paired-end Sequencing Library

The amplified product was diluted with 10 µl of EB buffer (QIAGEN) and used as a template for another round of PCR to incorporate a barcoded Illumina sequencing adaptor. PCR condition is as follows:

12.5 µl KAPA2G Robust HotStart ReadyMix (2×),

```
1.25 µl P5_extention_to_end (10 µM)
(5'-AATGATACGGCGACCACCGAGATCTACAC-3' (SEQ ID NO:
7)), 1.25 µl P7_i7_D701) (10 µM)
(5'-CAAGCAGAAGACGGCATACGAGATATTACTCGGTGACTGGAGTTC
AGACGTGTGC-3' (SEQ ID NO: 8)),
``` and water was added to make up 25 µl.

PCR program:

| | |
|---|---|
| 95° C. 5 min | |
| 95° C. 40 s | 5 Cycles |
| 61° C. 15 s | |
| 72° C. 15 s | |
| 72° C. 30 s | |
| 4° C. Hold | |

In order to destroy the "bubble products" due to over-amplification, an one-round PCR was performed as follows: an equal volume of KAPA2G Robust HotStart ReadyMix (2×), P5_extention_to_end (10 µM), P7_i7_D701 (10 µM) and water were further added to the PCR tube to make the final volume 50 µl. The cycling program was: 95° C.80s, 60° C.30s, 72° C.2 min, and hold at 4° C. The product was treated with 1.1×AMPure Beads. The library was eluted with 30 µl of EB buffer and selected by Pippin Prep (Sage Science) for the size between 320 bp 550 bp. Agilent 2100 Bioanalyzer with High Sensitivity DNA Kit (Agilent Technologies) and KAPA Library Quantification Kit Illumina platforms (KAPA Biosystems, KK4824) were used to test the quality of the library, before the HAT-seq library was subjected to paired-end sequencing (2×150 bp) using HiSeq2500 (Illumina).

Step 5: Identifying and Classifying the Genomic Location of the DNA Fragments

First, the DNA fragment sequences obtained by high-throughput sequencing were filtered using the sequence information of the transposon, and the DNA fragments from the target transposon family were retained. These DNA fragments were then aligned with human reference genomic sequences to determine the positions of the DNA fragments on the genome. For the present example, the ACC1 individual was compared with another healthy subject 2 (a healthy adult from the laboratory, sample code ZBX) by constructing a HAT-seq library, and 64 ACC1-specific germline insertions were identified.

Step 6: Verifying Results

By 3' PCR, whether the above-identified ACC1 specific insertions were present in the unrelated healthy subject 2 (from a healthy adult in the laboratory, sample code ZBX) was determined.

Figure 4A:
FIGS. 4A and 4B are validations of the ACC1 individual-specific insertions detected in Example 1. ACC1 non-reference germline insertions were amplified by 3' junction PCR experiments using both ACC1 and ZBX genomic DNA. An insertion that is only present in ACC1 but not ZBX is defined as an ACC1-specific insertion.
Figure 4B:
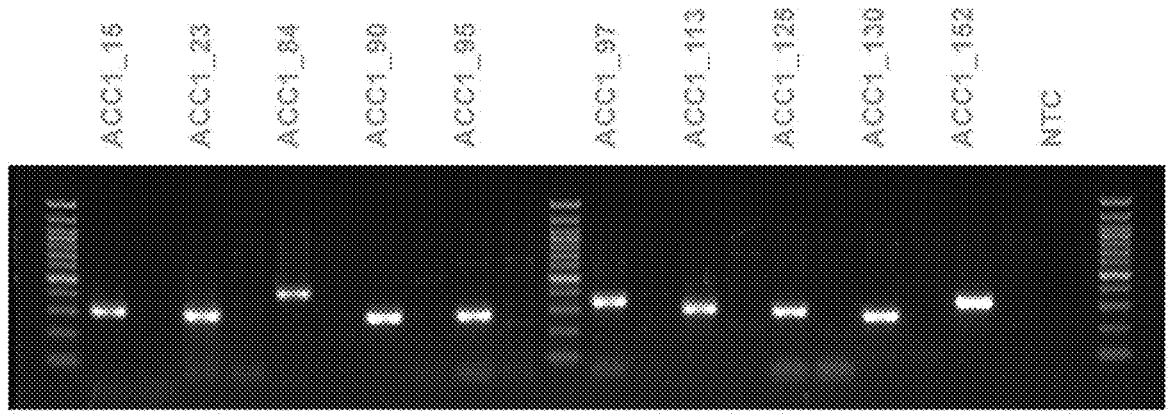

The results are shown in FIG. 4. In FIG. 4A, lane A represents the signal from the ACC1 individual, lane Z represents the signal from the ZBX individual, and NTC is the negative control. The identified ACC1 specific insertions do not have corresponding signals in the ZBX individuals. The numbering of the verified ACC1 specific insertion event is indicated in FIG. 4B.

The above results indicate that the specific transposon insertion events in the sample can be efficiently identified by HAT-seq method described above.

According to the above classification for the transposon insertion events, the numbers of DNA fragments produced by the endogenous germline insertion and the de novo insertions are calculated, respectively. The relative copy number of the de novo insertions in the sample is calculated using the endogenous germline insertions of DNA fragments as an internal reference. Since the copy number of endogenous germline insertions in the sample can be determined, the occurrence frequency of de novo insertions in each cell can be calculated. Finally, the transposon copy number and genomic position information in the test sample are output.

Example 2 Testing the Limit of Detection of the Method Using a Positive Control

In order to detect the Limit of Detection (LOD) of the HAT-seq method, the ACC1 specific insertion identified in Example 1 was used as a target. The genomic DNA sample of ACC1 was mixed into the ZBX sample with 1%, 0.1%, and 0.01% percentage, respectively. The ACC1 specific insertions in the mixed samples were used to mimic a de novo insertions occurring at different frequencies.

The analysis was carried out in accordance with the method described in Example 1 using 20 ng of mixed DNA with adaptor (corresponding to approximately 3000 cells) as a template.

Figure 7:
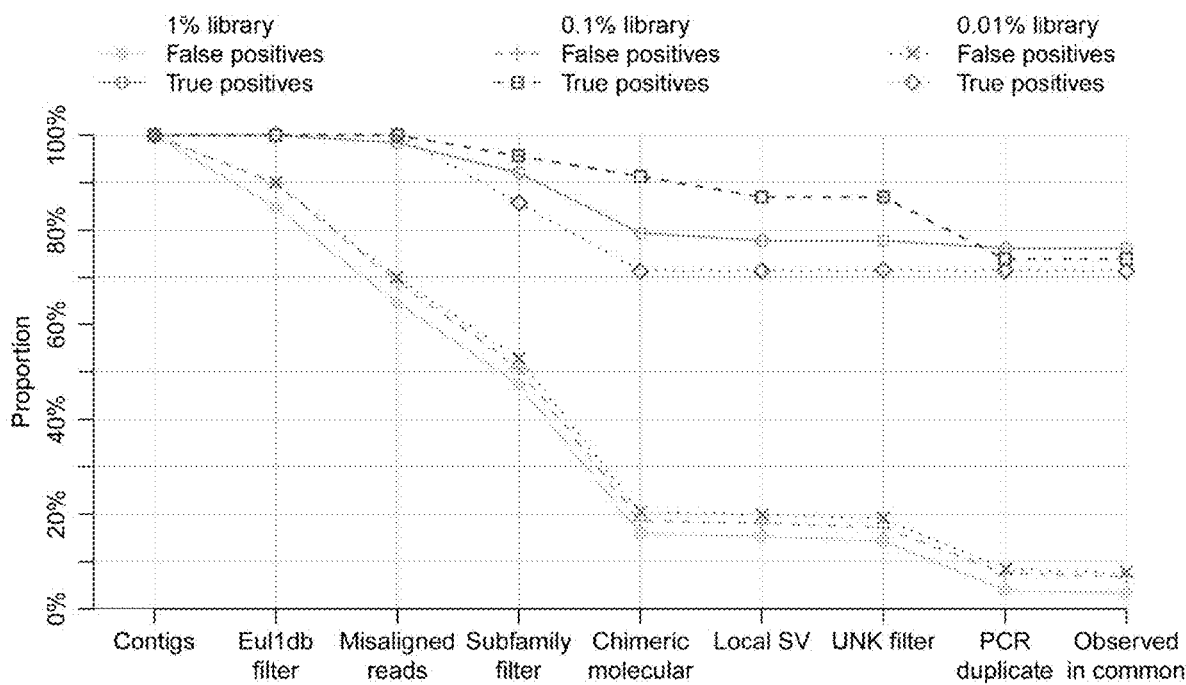
FIG. 7 is a schematic diagram of the efficiency of bioinformatics analysis filters. In the positive control experiments with different spike-in concentration gradients, the ratios after passing through the respective filters are counted for the known ACC1 specific insertions and all candidate somatic insertions, respectively. Each filter is described in Table 1. The known ACC1 specific insertions in the library are regarded as true positive sites, and the remaining insertion signals are regarded as false positive sites. In the 1%, 0.1%, and 0.01% concentration libraries, 76.18%, 73.91%, and 71.43% true positive sites are eventually retained. In contrast, 5.65%, 7.48%, and 7.88% of the false positive sites are eventually retained in the candidate somatic cell inserts, respectively.

In order to further improve the detection accuracy, a signal filter as shown in Table 1 was developed to reduce false positive signals such as chimeric molecules introduced during the PCR amplification during library construction. These technical errors are classified as non-specific amplification, chimeric molecule, errors of reads mapping, and systematic random errors. The results showed that in the samples containing 1% positive control library, all 64 ACC1 specific insertions were detected, 49 (76.6%) of which successfully passed all criteria of the filter. In the samples containing 0.1% positive control library, 23 out of all 64 ACC1 specific insertions were detected, 17 (73.9%) of which successfully passed all criteria of the filter. In the samples containing 0.1% positive control library, 7 out of all 64 ACC1 specific insertions were detected, 5 (71.4%) of which successfully passed all criteria of the filter. The results are shown in FIG. 7.

Figure 6A:
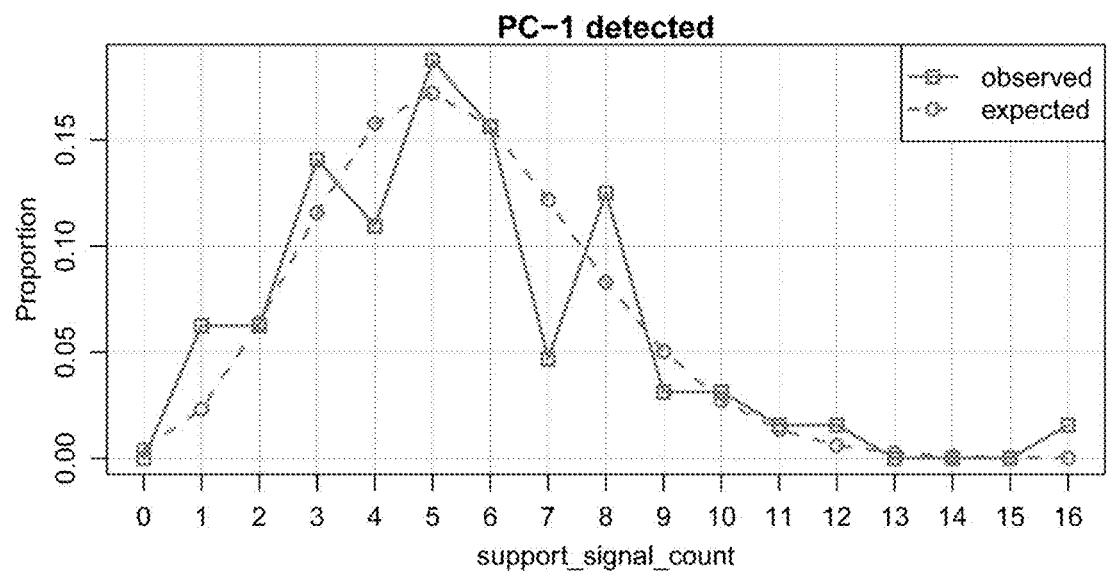
FIG. 6 is a schematic representation of the Poisson distribution for the identification of ACC1 specific insertion using HAT-seq. ACC1-specific insertions are identified using HAT-seq, and the number of insertion support signals detected in the positive control experiments with different spike-in concentrations is consistent with the Poisson distribution. The X axis represents the number of support signals in a certain site, and the Y axis represents the proportion. The squares represent the actual observations and the circles represent the Poisson distributions fitted using the Maximum Likelihood Estimation (MLE). The results show that each ACC1 specific insertion has a similar probability to be detected by random sampling.
Figure 6B:
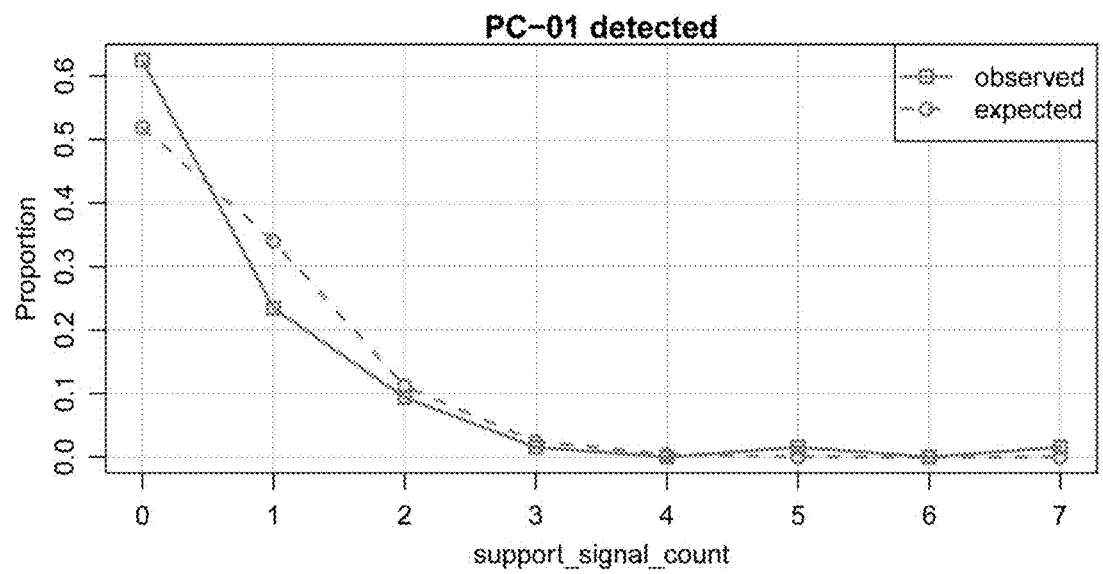
Figure 6C:
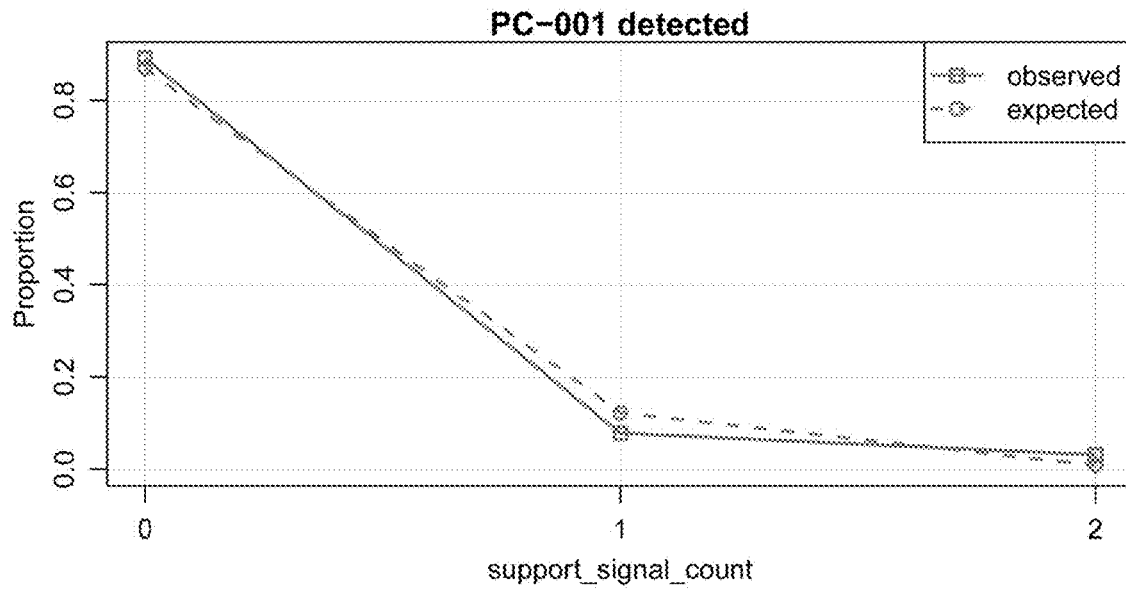

The data of the positive control library conformed to the Poisson distribution as shown in FIG. 6. Theoretically, according to the Poisson distribution, the libraries with 1%, 0.1%, and 0.01% concentration should have 64, 60.81, and 16.59 ACC1 specific insertions, respectively, which were randomly sampled and subsequently used as the starting template for the library. Therefore, based on the number of ACC1 specific insertions actually identified in libraries with different concentrations, the sensitivity for the libraries at 1%, 0.1%, and 0.01% concentration was estimated to be 76.6% (49/64) and 28% (Ser. No. 17/60.81), and 30.1% (5/16.59), respectively. For the library with 0.01% concentration, the observed values were compared to the expected values of the Poisson distribution, as shown in Table 2. The experimental data shows that the HAT-seq limit of detection reaches the level of single event, that is, as long as a signal exists in a library template, it can be detected in the final HAT-seq library data, with signal support. In the data shown in Table 2, some single copy templates were put in but not detected. This is because there is only one copy of each sequence, and there could be an inevitable signal loss during the random sampling process of library construction, size selection, and sequencing.

Figure 5:
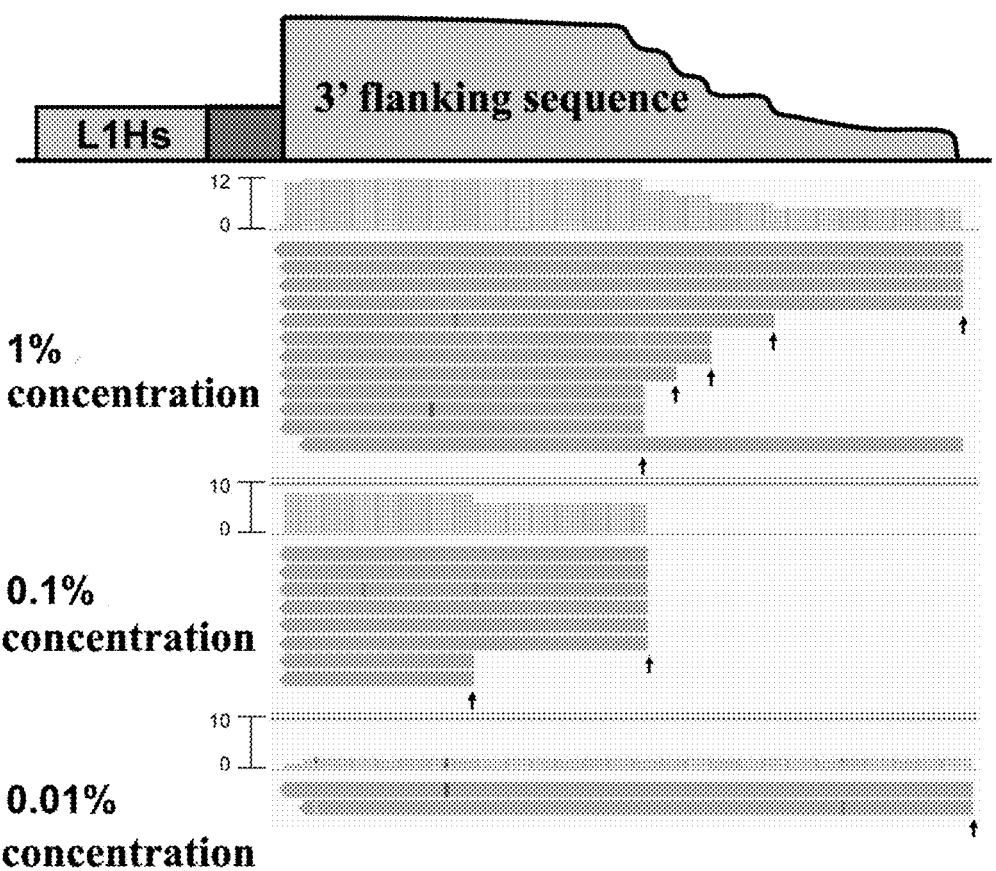
FIG. 5 is the validation result in Example 2 for the detection limit of the present invention. For the representative ACC1_132 specific insertion site, the support signals are shown in the HAT-seq positive control libraries with known spike-in concentrations of 1%, 0.1%, and 0.01%. With the decreasing of the spike-in concentration, the number of support signals is 5, 2, and 1, respectively. Single base substitution mutations in the sequence are indicated by light colors. The coverage depth of the regional single base resolution is illustrated by the upper gray histogram. The fragmented breakpoint of ACC1_132 insertion supporting reads are marked with arrows.

This demonstrates that the transposition event can be identified by the HAT-seq method with extremely high limit of detection, so that the somatic insertion event with extremely low incidence can be effectively identified and characterized. FIG. 5 is a graphical representation of the results of a representative insertion site numbered ACC1_132. ACC1_132 is the forward insertion of transposon L1 and therefore appears in the library data as being reversely mapped to the reference genome, i.e. a left arrow. The end of the left arrow is the insertion breakpoint, as indicated by the down arrow. The different starting sites on the right represent different support signals, i.e. different breakpoints in the 3' flanking sequence of the original insertion site template. In the library at 1% concentration, the ACC1_132 signal arrow has five different right starting sites, indicating that signals from at least five different templates in the library were detected. In the library at 0.1% concentration, the ACC1_132 signal arrow has two different right starting sites, indicating that signals from at least two different templates in the library were detected. Even in the library at 0.01% concentration, the ACC1_132 signal was still detected from one template. This indicates that its limit of detection enables the detection for a single insertion event.

TABLE 1

| Filters used in the somatic mutation identification process | |
|---|---|
| Name | Descriptions |
| Length of Unique Map | Length of a unique mapped reads less than 30 bp will be filtered out. |
| Number of Misaligned base | Unique map containing more than 3 misaligned bases will be filtered out. |
| Subfamily Specific Base | Sequence without the L1Hs subfamily specific G will be filtered out. |
| L1 Internal Chimeric Molecule | Sequence containing more than 4 mismatched bases in the 3' terminal sequence of L1Hs will be filtered out. |
| Poly(A) Internal Chimeric Molecule | Internal chimeric molecule formed in Poly(A) will be filtered out. Using BLAST to map Contig to hg19 and identifying the sequence between transposon and non-transposon. If the overlapping part > 10bp and A% >= 50%, or the overlapping part is 6-10 bp and A% < 50%, the sequence will be filtered out. |
| Known L1 Family Insertion | Somatic insertions overlapping with any L1 subfamilies on the reference genome will be filtered out. |
| Known Non-reference Genomic Insertion | Somatic insertions overlapping with L1 insertions in non-reference genome in the euL 1 db database will be filtered out. |
| Mapping Error | Sequence with the risk of being mapping errors will be filtered out, which is defined as inconsistency between the result of BWA and the result of BLAT. |
| Local Structural Variation | To filter the L1Hs insertions risky of coming from adjacent reference genomic, the sequence 2 kb downstream of the insertion site of the somatic is extracted and contig is mapped back to the region using BLAT to determine whether it is caused by a local structural variation. |
| Observed in Common | Somatic insertions present in two or more individuals will be filtered out. |
| PCR Duplicate | Somatic insertions not supported by PCR duplicate signals will be filtered out. |

Note: Among the 64 ACC1-specific positive control sites, in the 0.01% library, according to the Poisson distribution (λ=0.3), there are 2.36 sites with two or more copies and 14.22 sites with one. copy. In the 0.01% library, two sites with two or more signal supports are detected, together with five sites with one signal support.

---

What is claimed is:

1. A method of detecting genomic location of a transposon in a subject, comprising
   a) providing isolated DNA sample from a test sample of the subject;
   b) fragmenting the DNA sample to obtain DNA fragments;
   c) ligating adaptors to both ends of the DNA fragments to obtain a transposon-adaptor library;
   d) amplifying the transposon-adaptor library with primers comprising a first primer and a second primer, wherein the first primer comprises a transposon specific sequence capable of hybridizing to an internal sequence of the transposon, a second primer comprises an adapting sequence capable of hybridizing to the adaptor, thereby amplifying the transposon and flanking sequences thereof;
   e) sequencing the obtained product from amplification to obtain the flanking sequences; and
   f) aligning the obtained flanking sequences with a reference genomic sequence to obtain genomic location and orientation of the transposon; and
   wherein the first primer is a primer set comprising 3 or more different first primers, wherein each of the first primer further comprises a library adapting sequence at its 5' end and a spacer region is provided between the library adapting sequence and the transposon sequence, and wherein the length of the spacer region in each first primer is different.

2. The method according to claim 1, wherein the transposon specific sequence is capable of hybridizing with the internal sequence adjacent to the 3' or 5' end of the transposon.

3. The method according to claim 2, wherein the transposon specific sequence covers and binds to a specific nucleotide sequence or motif of a target transposon family.

4. The method according to claim 1, wherein the length of the spacer region in each first primer is independently 1, 2, 3, 4, 5, 6, 7, 8, 9 or 10 nucleotides.

5. The method according to claim 1, wherein steps a) to d) are carried out in same container.

6. The method according to claim 1, wherein the transposon is LINE-1 transposon.

7. The method according to claim 1, wherein the reference location is the transposon location in the reference genome for identifying germline transposon insertion.

8. The method according to claim 1, wherein the reference location is the transposon location in a control tissue or cell from the same individual for identifying somatic transposon insertion in the individual.

9. The method according to claim 1, wherein the test sample is a stem cell, including but not limited to embryonic stem cells and neural stem cells; somatic cells, including but not limited to liver cells, heart cells and brain cells; blood leukocytes; nerve cells, including but not limited to neural progenitor cells, neurons, peripheral nerve cells; germ cells, including but not limited to oocytes, spermatocytes, eggs and sperms; or disease-related cells, including but not limited to tumor cells, circulating tumor cells, and DNA derived from such cells, such as circulating tumor DNA.

10. The method according to claim 8, wherein the control cells are cells derived from liver, heart, brain, spleen, colon, skin, mucous membrane, hair follicle, blood leukocyte or saliva.

11. The method according to claim 1, wherein the test cells or control cells are mammalian cells.

12. The method according to claim 1, for use in diagnosing diseases.

13. The method according to claim 1, further comprising a step of identifying a tissue or cell specific transposon insertion event by, after step f), performing a step of g) comparing the location obtained in step f) with a reference location to identify the transposon which is present in step f) but absent in the reference location as the specific transposon insertion event in the test sample.

14. The method according to claim 13, further comprising a step of quantifying the tissue or cell specific transposon insertion event in the subject by, after step g), performing a step of h) counting the tissue or cell specific transposon insertion event in the sequencing data of the library to obtain a first number and transposon insertion events in the reference genome to obtain a second number corresponding to the subject, and calculating the ratio of the two numbers to quantify the tissue or cell specific transposon insertion event.

15. The method according to claim 1, wherein the length of the spacer region in each first primer is independently 1, 2, 3, 4, 5, 6, 7, 8, 9, 10, 11, 12, 13, 14, 15, 16, 17, 18, 19 or 20 nucleotides.

16. The method according to claim 12, wherein the disease is selected from the group consisting of nervous system diseases, cancer, proliferative disease, and brain organic lesion.

17. The method according to claim 16, wherein the nervous system disease is selected from the group consisting of Alzheimer's disease, Rett Syndrome, Schizophrenia, Bipolar disorder, and Autism spectrum disorder.

18. The method according to claim 16, wherein the cancer is selected from the group consisting of colon cancer, prostate cancer, ovarian cancer, multiple myeloma, glioblastoma, gastrointestinal cancer, pancreatic ductal adenocarcinoma, esophageal carcinoma, and hepatocellular carcinoma.

19. The method according to claim 16, wherein the proliferative disease is selected from the group consisting of Proteus syndrome, Ollier's disease, Maffucci syndrome, CLOVES syndrome, Schimmelpenning syndrome, and Sturge-Weber syndrome or the brain organic lesion is Hemimegalencephaly.

* * * * *

SEQUENCE LISTING

<160> NUMBER OF SEQ ID NOS: 11

<210> SEQ ID NO 1
<211> LENGTH: 33
<212> TYPE: DNA
<213> ORGANISM: Artificial Sequence
<220> FEATURE:
<223> OTHER INFORMATION: synthetic primer
<220> FEATURE:
<221> NAME/KEY: modified base
<222> LOCATION: (33)..(33)
<223> OTHER INFORMATION: phosphorothioate modification

<400> SEQUENCE: 1
acactctttc cctacacgac gctcttccga tct        33

<210> SEQ ID NO 2
<211> LENGTH: 14
<212> TYPE: DNA
<213> ORGANISM: Artificial Sequence
<220> FEATURE:
<223> OTHER INFORMATION: synthetic primer
<220> FEATURE:
<221> NAME/KEY: modified base
<222> LOCATION: (1)..(1)
<223> OTHER INFORMATION: phosphate modification
<220> FEATURE:
<221> NAME/KEY: modified base
<222> LOCATION: (13)..(14)
<223> OTHER INFORMATION: phosphorothioate modification

<400> SEQUENCE: 2
gatcggaaga gcac        14

<210> SEQ ID NO 3
<211> LENGTH: 47
<212> TYPE: DNA
<213> ORGANISM: Artificial Sequence
<220> FEATURE:
<223> OTHER INFORMATION: synthetic primer

<400> SEQUENCE: 3
aatgatacgg cgaccaccga gatctacact ctttccctac acgacgc        47

<210> SEQ ID NO 4
<211> LENGTH: 64
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(36)
<223> OTHER INFORMATION: n is a,t,c or g
<220> FEATURE:
<221> NAME/KEY: modified base
<222> LOCATION: (63)..(64)
<223> OTHER INFORMATION: phosphorothioate modification

<400> SEQUENCE: 4
gtgactggag ttcagacgtg tgctcttccg atctnnggga gatataccta atgctagatg        60
acac        64

<210> SEQ ID NO 5
<211> LENGTH: 66
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(38)
<223> OTHER INFORMATION: n is a,t,c or g
<220> FEATURE:
<221> NAME/KEY: modified base
<222> LOCATION: (65)..(66)
<223> OTHER INFORMATION: phosphorothioate modification

<400> SEQUENCE: 5
gtgactggag ttcagacgtg tgctcttccg atctnnnngg gagatatacc taatgctaga    60
tgacac                                                               66

<210> SEQ ID NO 6
<211> LENGTH: 68
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(40)
<223> OTHER INFORMATION: n is a,t,c or g
<220> FEATURE:
<221> NAME/KEY: modified base
<222> LOCATION: (67)..(68)
<223> OTHER INFORMATION: phosphorothioate modification

<400> SEQUENCE: 6
gtgactggag ttcagacgtg tgctcttccg atctnnnnnn gggagatata cctaatgcta    60
gatgacac                                                             68

<210> SEQ ID NO 7
<211> LENGTH: 29
<212> TYPE: DNA
<213> ORGANISM: Artificial Sequence
<220> FEATURE:
<223> OTHER INFORMATION: synthetic primer

<400> SEQUENCE: 7
aatgatacgg cgaccaccga gatctacac                                      29

<210> SEQ ID NO 8
<211> LENGTH: 55
<212> TYPE: DNA
<213> ORGANISM: Artificial Sequence
<220> FEATURE:
<223> OTHER INFORMATION: synthetic primer

<400> SEQUENCE: 8
caagcagaag acggcatacg agatattact cggtgactgg agttcagacg tgtgc         55

<210> SEQ ID NO 9
<211> LENGTH: 64
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(36)

```
<223> OTHER INFORMATION: n is a, c, g, or t

<400> SEQUENCE: 9
gtgactggag ttcagacgtg tgctcttccg atctnnggga gatataccta atgctagatg     60
acac                                                                  64

<210> SEQ ID NO 10
<211> LENGTH: 66
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(38)
<223> OTHER INFORMATION: n is a, c, g, or t

<400> SEQUENCE: 10
gtgactggag ttcagacgtg tgctcttccg atctnnnngg gagatatacc taatgctaga    60
tgacac                                                                66

<210> SEQ ID NO 11
<211> LENGTH: 68
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(40)
<223> OTHER INFORMATION: n is a, c, g, or t

<400> SEQUENCE: 11
gtgactggag ttcagacgtg tgctcttccg atctnnnnnn gggagatata cctaatgcta    60
gatgacac                                                              68
```